United States Patent
Darling et al.

(10) Patent No.: US 8,741,841 B2
(45) Date of Patent: Jun. 3, 2014

(54) FIBROBLAST GROWTH FACTOR 21 PROTEINS

(71) Applicant: Eli Lilly and Company, Indianapolis, IN (US)

(72) Inventors: Ryan James Darling, Fishers, IN (US); Craig Duane Dickinson, San Diego, CA (US); David Albert Driver, Solana Beach, CA (US); Malgorzata Donata Gonciarz, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/910,149

(22) Filed: Jun. 5, 2013

(65) Prior Publication Data

US 2013/0330336 A1 Dec. 12, 2013

Related U.S. Application Data

(60) Provisional application No. 61/777,386, filed on Mar. 12, 2013, provisional application No. 61/658,104, filed on Jun. 11, 2012.

(51) Int. Cl.
| | |
|---|---|
| A61K 38/18 | (2006.01) |
| C12P 21/04 | (2006.01) |
| C12N 5/00 | (2006.01) |
| C07H 21/04 | (2006.01) |

(52) U.S. Cl.
USPC ........... 514/9.1; 530/350; 530/399; 435/69.7; 435/325; 536/23.4

(58) Field of Classification Search
CPC .... A61K 38/1825; C07K 14/50; C07K 19/00; C07K 2317/52; C07K 2319/30
See application file for complete search history.

(56) References Cited

U.S. PATENT DOCUMENTS

| | | | |
|---|---|---|---|
| 2009/0118190 A1* | 5/2009 | Beals et al. | 514/12 |
| 2011/0172401 A1* | 7/2011 | Cujec et al. | 530/399 |
| 2012/0177646 A1 | 7/2012 | Belouski et al. | |
| 2013/0085098 A1 | 4/2013 | Dickinson et al. | |

FOREIGN PATENT DOCUMENTS

| | | |
|---|---|---|
| EP | 1218509 | 4/2009 |
| EP | 2189475 | 5/2010 |
| WO | 03011213 | 2/2003 |
| WO | 2005061712 | 7/2005 |
| WO | 2005113606 A2 | 12/2005 |
| WO | 2008121563 | 10/2008 |
| WO | 2009149171 | 12/2009 |
| WO | 2010042747 | 4/2010 |
| WO | 2010065439 | 6/2010 |
| WO | 2010084169 | 7/2010 |
| WO | 2010129503 | 11/2010 |
| WO | 2010129600 | 11/2010 |

OTHER PUBLICATIONS

Berglund, Eric D., et al., Fibroblast Growth Factor 21 Controls Glycemia Via Regulation of Hepatic Glucose Flux and Insulin Sensitivity, Endocrinology, Sep. 2009, 150 (9), pp. 4084-4093.

Kharitonenkov, Alexei, et al., FGF-21 as a Novel Metabolic Regulator, J. Clin. Invest., 2005, 115 (6), pp. 1627-1635.

Kharitonenkov, Alexei, et al., The Metabolic State of Diabetic Monkeys is Regulated by Fibroblast Growth Factor-21, Endocrinology, 2007, 148 (2), pp. 774-781.

Kharitonenkov, Alexei, et al., Fibroblast Growth Factor-21 as a Therapeutic Agent for Metabolic Diseases, Biodrugs, 2008, 22 (1), pp. 37-44.

Micanovic, Radmila, et al., Different Roles of N- and C-Termini in the Functional Activity of FGF21, J. Cell. Physiol. 2009, 219: pp. 227-234.

Wente, Wolf, et al., Fibroblast Growth Factor-21 Improves Pancreatic β-Cell Function and Survival by Activation of Extracellular Signal-Reglated Kinase ½ and Akt Signaling Pathways, Diabetes, 2006, 55, pp. 2470-2478.

Wu, Xinle, et al., C-Terminal Tail of FGF19 Determines Its Specificity Toward Klotho Co-Receptors, J. Biol. Chem., Nov. 28, 2008, vol. 283, No. 48, pp. 33304-33309.

Yie, Junming, et al., FGF21 N- and C-Termini Play Different Roles in Receptor Interaction and Activation, FEBS Letters, 2009, 583 pp. 19-24.

* cited by examiner

*Primary Examiner* — Marianne P Allen
(74) *Attorney, Agent, or Firm* — Robert B. Johnson; Andrea M. Castetter

(57) ABSTRACT

This present invention relates to pharmacologically potent and stable human fibroblast growth factor 21 (FGF21) proteins, pharmaceutical compositions comprising FGF21 proteins, and methods for treating type 2 diabetes, obesity, dyslipidemia, and/or metabolic syndrome using such proteins.

10 Claims, No Drawings

SEQUENCE LISTING

```
<160> NUMBER OF SEQ ID NOS: 15

<210> SEQ ID NO 1
<211> LENGTH: 180
<212> TYPE: PRT
<213> ORGANISM: Artificial Sequence
<220> FEATURE:
<223> OTHER INFORMATION: synthetic construct

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Asp Leu Lys Glu Asp Gly Tyr Asn Val Tyr Gln Ser Glu Ala His
            100                 105                 110
```

```
Gly Leu Pro Leu His Leu Pro Gly Asp Lys Ser Pro His Arg Lys Pro
            115                 120                 125
Ala Pro Arg Gly Pro Ala Arg Phe Leu Pro Leu Pro Gly Leu Pro Pro
    130                 135                 140
Ala Leu Pro Glu Pro Pro Gly Ile Leu Ala Pro Gln Pro Pro Asp Val
145                 150                 155                 160
Gly Ser Ser Asp Pro Leu Arg Leu Val Glu Pro Ser Gln Leu Arg Ser
                165                 170                 175
Pro Ser Phe Glu
            180

<210> SEQ ID NO 2
<211> LENGTH: 181
<212> TYPE: PRT
<213> ORGANISM: Homo sapiens

<400> SEQUENCE: 2

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Ala His
            20                  25                  30
Leu Glu Ile Arg Glu Asp Gly Thr Val Gly Gly Ala Ala Asp Gln Ser
        35                  40                  45
Pro Glu Ser Leu Leu Gln Leu Lys Ala Leu Lys Pro Gly Val Ile Gln
    50                  55                  60
Ile Leu Gly Val Lys Thr Ser Arg Phe Leu Cys Gln Arg Pro Asp Gly
65                  70                  75                  80
Ala Leu Tyr Gly Ser Leu His Phe Asp Pro Glu Ala Cys Ser Phe Arg
                85                  90                  95
Glu Leu Leu Leu Glu Asp Gly Tyr Asn Val Tyr Gln Ser Glu Ala His
            100                 105                 110
Gly Leu Pro Leu His Leu Pro Gly Asn Lys Ser Pro His Arg Asp Pro
        115                 120                 125
Ala Pro Arg Gly Pro Ala Arg Phe Leu Pro Leu Pro Gly Leu Pro Pro
    130                 135                 140
Ala Leu Pro Glu Pro Pro Gly Ile Leu Ala Pro Gln Pro Pro Asp Val
145                 150                 155                 160
Gly Ser Ser Asp Pro Leu Ser Met Val Gly Pro Ser Gln Gly Arg Ser
                165                 170                 175
Pro Ser Tyr Ala Ser
            180

<210> SEQ ID NO 3
<211> LENGTH: 19
<212> TYPE: PRT
<213> ORGANISM: Artificial Sequence
<220> FEATURE:
<223> OTHER INFORMATION: synthetic construct

<400> SEQUENCE: 3

Met Arg Leu Ala Val Gly Ala Leu Leu Val Cys Ala Val Leu Gly Leu
1               5                   10                  15
Cys Leu Ala

<210> SEQ ID NO 4
<211> LENGTH: 23
<212> TYPE: PRT
<213> ORGANISM: Artificial Sequence
```

```
<220> FEATURE:
<223> OTHER INFORMATION: synthetic construct

<400> SEQUENCE: 4

Met Lys Ile Cys Ser Leu Thr Leu Leu Ser Phe Leu Leu Leu Ala Ala
1               5                   10                  15

Gln Val Leu Leu Val Glu Gly
            20

<210> SEQ ID NO 5
<211> LENGTH: 424
<212> TYPE: PRT
<213> ORGANISM: Artificial Sequence
<220> FEATURE:
<223> OTHER INFORMATION: synthetic construct

<400> SEQUENCE: 5

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Gly Ser Gly Gly Gly
225                 230                 235                 240

Gly Ser Ala His Pro Ile Pro Asp Ser Ser Pro Leu Leu Gln Phe
                245                 250                 255

Gly Gly Gln Val Arg Gln Arg Tyr Leu Tyr Thr Asp Asp Ala Gln Gln
            260                 265                 270

Thr Glu Cys His Leu Glu Ile Arg Glu Asp Gly Thr Val Gly Cys Ala
        275                 280                 285

Ala Asp Gln Ser Pro Glu Ser Leu Leu Gln Leu Lys Ala Leu Lys Pro
    290                 295                 300

Gly Val Ile Gln Ile Leu Gly Val Lys Thr Ser Arg Phe Leu Cys Gln
305                 310                 315                 320
```

```
Arg Pro Asp Gly Ala Leu Tyr Gly Ser Leu His Phe Asp Pro Glu Ala
                325                 330                 335

Cys Ser Phe Arg Glu Asp Leu Lys Glu Asp Gly Tyr Asn Val Tyr Gln
            340                 345                 350

Ser Glu Ala His Gly Leu Pro Leu His Leu Pro Gly Asp Lys Ser Pro
        355                 360                 365

His Arg Lys Pro Ala Pro Arg Gly Pro Ala Arg Phe Leu Pro Leu Pro
    370                 375                 380

Gly Leu Pro Pro Ala Leu Pro Glu Pro Gly Ile Leu Ala Pro Gln
385                 390                 395                 400

Pro Pro Asp Val Gly Ser Ser Asp Pro Leu Arg Leu Val Glu Pro Ser
                405                 410                 415

Gln Leu Arg Ser Pro Ser Phe Glu
            420

<210> SEQ ID NO 6
<211> LENGTH: 424
<212> TYPE: PRT
<213> ORGANISM: Artificial Sequence
<220> FEATURE:
<223> OTHER INFORMATION: synthetic construct

<400> SEQUENCE: 6

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Ser Gly Gly
225                 230                 235                 240

Gly Gly Ser Ala His Pro Ile Pro Asp Ser Ser Pro Leu Leu Gln Phe
                245                 250                 255
```

```
Gly Gly Gln Val Arg Gln Arg Tyr Leu Tyr Thr Asp Asp Ala Gln Gln
            260                 265                 270

Thr Glu Cys His Leu Glu Ile Arg Glu Asp Gly Thr Val Gly Cys Ala
275                 280                 285

Ala Asp Gln Ser Pro Glu Ser Leu Leu Gln Leu Lys Ala Leu Lys Pro
        290                 295                 300

Gly Val Ile Gln Ile Leu Gly Val Lys Thr Ser Arg Phe Leu Cys Gln
305                 310                 315                 320

Arg Pro Asp Gly Ala Leu Tyr Gly Ser Leu His Phe Asp Pro Glu Ala
                325                 330                 335

Cys Ser Phe Arg Glu Asp Leu Leu Glu Asp Gly Tyr Asn Val Tyr Gln
            340                 345                 350

Ser Glu Ala His Gly Leu Pro Leu His Leu Pro Gly Asp Lys Ser Pro
        355                 360                 365

His Arg Lys Pro Ala Pro Arg Gly Pro Ala Arg Phe Leu Pro Leu Pro
    370                 375                 380

Gly Leu Pro Pro Ala Leu Pro Glu Pro Pro Gly Ile Leu Ala Pro Gln
385                 390                 395                 400

Pro Pro Asp Val Gly Ser Ser Asp Pro Leu Arg Leu Val Glu Pro Ser
                405                 410                 415

Gln Leu Arg Ser Pro Ser Phe Glu
            420

<210> SEQ ID NO 7
<211> LENGTH: 424
<212> TYPE: PRT
<213> ORGANISM: Artificial Sequence
<220> FEATURE:
<223> OTHER INFORMATION: synthetic construct

<400> SEQUENCE: 7

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
```

```
                    195                 200                 205
Val Met His Glu Ala Leu His Asn His Tyr Thr Gln Lys Ser Leu Ser
    210                 215                 220

Leu Ser Leu Gly Gly Gly Gly Ser Gly Gly Gly Ser Gly Gly
225                 230                 235                 240

Gly Gly Ser Ala His Pro Ile Pro Asp Ser Ser Pro Leu Leu Gln Phe
                245                 250                 255

Gly Gly Gln Val Arg Gln Arg Tyr Leu Tyr Thr Asp Asp Ala Gln Gln
            260                 265                 270

Thr Glu Cys His Leu Glu Ile Arg Glu Asp Gly Thr Val Gly Cys Ala
        275                 280                 285

Ala Asp Gln Ser Pro Glu Ser Leu Leu Gln Leu Lys Ala Leu Lys Pro
    290                 295                 300

Gly Val Ile Gln Ile Leu Gly Val Lys Thr Ser Arg Phe Leu Cys Gln
305                 310                 315                 320

Arg Pro Asp Gly Ala Leu Tyr Gly Ser Leu His Phe Asp Pro Glu Ala
                325                 330                 335

Cys Ser Phe Arg Glu Leu Leu Lys Glu Asp Gly Tyr Asn Val Tyr Gln
            340                 345                 350

Ser Glu Ala His Gly Leu Pro Leu His Leu Pro Gly Asp Lys Ser Pro
        355                 360                 365

His Arg Lys Pro Ala Pro Arg Gly Pro Ala Arg Phe Leu Pro Leu Pro
    370                 375                 380

Gly Leu Pro Pro Ala Leu Pro Glu Pro Gly Ile Leu Ala Pro Gln
385                 390                 395                 400

Pro Pro Asp Val Gly Ser Ser Asp Pro Leu Arg Leu Val Glu Pro Ser
                405                 410                 415

Gln Leu Arg Ser Pro Ser Phe Glu
            420

<210> SEQ ID NO 8
<211> LENGTH: 425
<212> TYPE: PRT
<213> ORGANISM: Artificial Sequence
<220> FEATURE:
<223> OTHER INFORMATION: synthetic construct

<400> SEQUENCE: 8

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140
```

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Ser Gly Gly Gly Gly
225                 230                 235                 240

Gly Gly Ser Ala His Pro Ile Pro Asp Ser Ser Pro Leu Leu Gln Phe
                245                 250                 255

Gly Gly Gln Val Arg Gln Arg Tyr Leu Tyr Thr Asp Asp Ala Gln Gln
            260                 265                 270

Thr Glu Cys His Leu Glu Ile Arg Glu Asp Gly Thr Val Gly Cys Ala
        275                 280                 285

Ala Asp Gln Ser Pro Glu Ser Leu Leu Gln Leu Lys Ala Leu Lys Pro
    290                 295                 300

Gly Val Ile Gln Ile Leu Gly Val Lys Thr Ser Arg Phe Leu Cys Gln
305                 310                 315                 320

Arg Pro Asp Gly Ala Leu Tyr Gly Ser Leu His Phe Asp Pro Glu Ala
                325                 330                 335

Cys Ser Phe Arg Glu Asp Leu Leu Glu Asp Gly Tyr Asn Val Tyr Gln
            340                 345                 350

Ser Glu Ala His Gly Leu Pro Leu His Leu Pro Gly Asp Lys Ser Pro
        355                 360                 365

His Arg Lys Pro Ala Pro Arg Gly Pro Ala Arg Phe Leu Pro Leu Pro
    370                 375                 380

Gly Leu Pro Pro Ala Leu Pro Glu Pro Gly Ile Leu Ala Pro Gln
385                 390                 395                 400

Pro Pro Asp Val Gly Ser Ser Asp Pro Leu Arg Leu Val Glu Pro Ser
                405                 410                 415

Gln Leu Leu Ser Pro Ser Phe Leu Gly
            420                 425

<210> SEQ ID NO 9
<211> LENGTH: 425
<212> TYPE: PRT
<213> ORGANISM: Artificial Sequence
<220> FEATURE:
<223> OTHER INFORMATION: synthetic construct

<400> SEQUENCE: 9

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Gly Gly Gly Ser Gly Gly Gly Ser Gly Gly
225                 230                 235                 240

Gly Gly Ser Ala His Pro Ile Pro Asp Ser Ser Pro Leu Leu Gln Phe
            245                 250                 255

Gly Gly Gln Val Arg Gln Arg Tyr Leu Tyr Thr Asp Asp Ala Gln Gln
            260                 265                 270

Thr Glu Cys His Leu Glu Ile Arg Glu Asp Gly Thr Val Gly Cys Ala
            275                 280                 285

Ala Asp Gln Ser Pro Glu Ser Leu Leu Gln Leu Lys Ala Leu Lys Pro
290                 295                 300

Gly Val Ile Gln Ile Leu Gly Val Lys Thr Ser Arg Phe Leu Cys Gln
305                 310                 315                 320

Arg Pro Asp Gly Ala Leu Tyr Gly Ser Leu His Phe Asp Pro Glu Ala
            325                 330                 335

Cys Ser Phe Arg Glu Asp Leu Lys Glu Asp Gly Tyr Asn Val Tyr Gln
            340                 345                 350

Ser Glu Ala His Gly Leu Pro Leu His Leu Pro Gly Asp Lys Ser Pro
            355                 360                 365

His Arg Lys Pro Ala Pro Arg Gly Pro Ala Arg Phe Leu Pro Leu Pro
            370                 375                 380

Gly Leu Pro Pro Ala Leu Pro Glu Pro Pro Gly Ile Leu Ala Pro Gln
385                 390                 395                 400

Pro Pro Asp Val Gly Ser Ser Asp Pro Leu Arg Leu Val Glu Pro Ser
            405                 410                 415

Gln Leu Leu Ser Pro Ser Phe Leu Gly
            420                 425

<210> SEQ ID NO 10
<211> LENGTH: 5
<212> TYPE: PRT
<213> ORGANISM: Artificial Sequence
<220> FEATURE:
<223> OTHER INFORMATION: synthetic construct

<400> SEQUENCE: 10

Gly Gly Gly Gly Ser
1               5

```
<210> SEQ ID NO 11
<211> LENGTH: 16
<212> TYPE: PRT
<213> ORGANISM: Artificial Sequence
<220> FEATURE:
<223> OTHER INFORMATION: synthetic construct

<400> SEQUENCE: 11

Gly Gly Gly Gly Ser Gly Gly Gly Gly Ser Gly Gly Gly Gly Ser Ala
1               5                   10                  15

<210> SEQ ID NO 12
<211> LENGTH: 11
<212> TYPE: PRT
<213> ORGANISM: Artificial Sequence
<220> FEATURE:
<223> OTHER INFORMATION: synthetic construct

<400> SEQUENCE: 12

Gly Gly Gly Gly Ser Gly Gly Gly Gly Ser Ala
1               5                   10

<210> SEQ ID NO 13
<211> LENGTH: 1272
<212> TYPE: DNA
<213> ORGANISM: Artificial Sequence
<220> FEATURE:
<223> OTHER INFORMATION: synthetic construct

<400> SEQUENCE: 13
gagtccaaat atggtccccc atgcccaccc tgcccagcac ctgaggccgc cggggggacca      60
tcagtcttcc tgttcccccc aaaacccaag gacactctca tgatctcccg gacccctgag     120
gtcacgtgcg tggtggtgga cgtgagccag gaagaccccg aggtccagtt caactggtac     180
gtggatggcg tggaggtgca taatgccaag acaaagccgc gggaggagca gttcaacagc     240
acgtaccgtg tggtcagcgt cctcaccgtc ctgcaccagg actggctgaa cggcaaggag     300
tacaagtgca aggtctccaa caaaggcctc ccgtcctcca tcgagaaaac catctccaaa     360
gccaaagggc agccccgaga gccacaggtg tacaccctgc ccccatccca ggaggagatg     420
accaagaacc aggtcagcct gacctgcctg gtcaaaggct tctaccccag cgacatcgcc     480
gtggagtggg aaagcaatgg gcagccggag aacaactaca agaccacgcc tcccgtgctg     540
gactccgacg gctccttctt cctctacagc aggctaaccg tggacaagag caggtggcag     600
caggggaatg tcttctcatg ctccgtgatg catgaggctc tgcacaacca ctacacacag     660
aagagcctct ccctgtctct gggtggtggt ggtggctccg gaggcggcgg ctctggtggc     720
ggtggcagcg ctcaccccat ccctgactcc agtcctctcc tgcaattcgg ggccaagtc     780
cggcagcggt acctgtacac cgacgacgcc cagcagaccg agtgccacct ggaaatccgg     840
gaggacggca ccgtgggctg tgccgccgac cagtcccctg agtccctgct gcagctgaag     900
gccctgaagc ctggcgtgat ccagatcctg ggcgtgaaaa cctcccggtt cctgtgccag     960
aggcctgatg gcgccctgta cggctccctg cacttcgacc ctgaggcctg ctccttccgg    1020
gaggacctga aggaagatgg ctacaacgtg taccagtccg aggctcacgg cctgcctctg    1080
catctgcctg cgacaagtc cccccaccgg aagcctgctc ctaggggccc tgccagattc    1140
ctgccactgc ctggcctgcc tccagctctg cctgagcctg ctggcatcct ggcccctcag    1200
cctccagacg tgggctcctc cgaccctctg cggctggtcg agccttccca gctgcggagc    1260
cctagcttcg ag                                                        1272
```

-continued

```
<210> SEQ ID NO 14
<211> LENGTH: 228
<212> TYPE: PRT
<213> ORGANISM: Artificial Sequence
<220> FEATURE:
<223> OTHER INFORMATION: synthetic construct

<400> SEQUENCE: 14

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 15
<211> LENGTH: 425
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (342)..(342)
<223> OTHER INFORMATION: Xaa at position 342 is Leu or Asp
<220> FEATURE:
<221> NAME/KEY: MISC_FEATURE
<222> LOCATION: (344)..(344)
<223> OTHER INFORMATION: Xaa at position 344 is Leu or Lys
<220> FEATURE:
<221> NAME/KEY: MISC_FEATURE
<222> LOCATION: (419)..(419)
<223> OTHER INFORMATION: Xaa at position 419 is Arg or Leu
<220> FEATURE:
<221> NAME/KEY: MISC_FEATURE
<222> LOCATION: (424)..(424)
<223> OTHER INFORMATION: Xaa at position 424 is Leu or Glu
<220> FEATURE:
<221> NAME/KEY: MISC_FEATURE
<222> LOCATION: (425)..(425)
```

<223> OTHER INFORMATION: Xaa at position 425 is Gly or is absent

<400> SEQUENCE: 15

| | | | | | | | | | | | | | | |
|---|---|---|---|---|---|---|---|---|---|---|---|---|---|---|
| Glu | Ser | Lys | Tyr | Gly | Pro | Pro | Cys | Pro | Pro | Cys | Pro | Ala | Pro | Glu | Ala |
| 1 | | | | 5 | | | | | 10 | | | | | 15 | |
| Ala | Gly | Gly | Pro | Ser | Val | Phe | Leu | Phe | Pro | Pro | Lys | Pro | Lys | Asp | Thr |
| | | | 20 | | | | | 25 | | | | | 30 | | |
| Leu | Met | Ile | Ser | Arg | Thr | Pro | Glu | Val | Thr | Cys | Val | Val | Val | Asp | Val |
| | | 35 | | | | | 40 | | | | | 45 | | | |
| Ser | Gln | Glu | Asp | Pro | Glu | Val | Gln | Phe | Asn | Trp | Tyr | Val | Asp | Gly | Val |
| | 50 | | | | | 55 | | | | | 60 | | | | |
| Glu | Val | His | Asn | Ala | Lys | Thr | Lys | Pro | Arg | Glu | Glu | Gln | Phe | Asn | Ser |
| 65 | | | | | 70 | | | | | 75 | | | | | 80 |
| Thr | Tyr | Arg | Val | Val | Ser | Val | Leu | Thr | Val | Leu | His | Gln | Asp | Trp | Leu |
| | | | | 85 | | | | | 90 | | | | | 95 | |
| Asn | Gly | Lys | Glu | Tyr | Lys | Cys | Lys | Val | Ser | Asn | Lys | Gly | Leu | Pro | Ser |
| | | | 100 | | | | | 105 | | | | | 110 | | |
| Ser | Ile | Glu | Lys | Thr | Ile | Ser | Lys | Ala | Lys | Gly | Gln | Pro | Arg | Glu | Pro |
| | | 115 | | | | | 120 | | | | | 125 | | | |
| Gln | Val | Tyr | Thr | Leu | Pro | Pro | Ser | Gln | Glu | Glu | Met | Thr | Lys | Asn | Gln |
| | 130 | | | | | 135 | | | | | 140 | | | | |
| Val | Ser | Leu | Thr | Cys | Leu | Val | Lys | Gly | Phe | Tyr | Pro | Ser | Asp | Ile | Ala |
| 145 | | | | | 150 | | | | | 155 | | | | | 160 |
| Val | Glu | Trp | Glu | Ser | Asn | Gly | Gln | Pro | Glu | Asn | Asn | Tyr | Lys | Thr | Thr |
| | | | | 165 | | | | | 170 | | | | | 175 | |
| Pro | Pro | Val | Leu | Asp | Ser | Asp | Gly | Ser | Phe | Phe | Leu | Tyr | Ser | Arg | Leu |
| | | | 180 | | | | | 185 | | | | | 190 | | |
| Thr | Val | Asp | Lys | Ser | Arg | Trp | Gln | Glu | Gly | Asn | Val | Phe | Ser | Cys | Ser |
| | | 195 | | | | | 200 | | | | | 205 | | | |
| Val | Met | His | Glu | Ala | Leu | His | Asn | His | Tyr | Thr | Gln | Lys | Ser | Leu | Ser |
| | 210 | | | | | 215 | | | | | 220 | | | | |
| Leu | Ser | Leu | Gly | Gly | Gly | Gly | Ser | Gly | Gly | Gly | Ser | Gly | Gly | Gly | Gly |
| 225 | | | | | 230 | | | | | 235 | | | | | 240 |
| Gly | Gly | Ser | Ala | His | Pro | Ile | Pro | Asp | Ser | Ser | Pro | Leu | Leu | Gln | Phe |
| | | | | 245 | | | | | 250 | | | | | 255 | |
| Gly | Gly | Gln | Val | Arg | Gln | Arg | Tyr | Leu | Tyr | Thr | Asp | Asp | Ala | Gln | Gln |
| | | | 260 | | | | | 265 | | | | | 270 | | |
| Thr | Glu | Cys | His | Leu | Glu | Ile | Arg | Glu | Asp | Gly | Thr | Val | Gly | Cys | Ala |
| | | 275 | | | | | 280 | | | | | 285 | | | |
| Ala | Asp | Gln | Ser | Pro | Glu | Ser | Leu | Leu | Gln | Leu | Lys | Ala | Leu | Lys | Pro |
| | 290 | | | | | 295 | | | | | 300 | | | | |
| Gly | Val | Ile | Gln | Ile | Leu | Gly | Val | Lys | Thr | Ser | Arg | Phe | Leu | Cys | Gln |
| 305 | | | | | 310 | | | | | 315 | | | | | 320 |
| Arg | Pro | Asp | Gly | Ala | Leu | Tyr | Gly | Ser | Leu | His | Phe | Asp | Pro | Glu | Ala |
| | | | | 325 | | | | | 330 | | | | | 335 | |
| Cys | Ser | Phe | Arg | Glu | Xaa | Leu | Xaa | Glu | Asp | Gly | Tyr | Asn | Val | Tyr | Gln |
| | | | 340 | | | | | 345 | | | | | 350 | | |
| Ser | Glu | Ala | His | Gly | Leu | Pro | Leu | His | Leu | Pro | Gly | Asp | Lys | Ser | Pro |
| | | 355 | | | | | 360 | | | | | 365 | | | |
| His | Arg | Lys | Pro | Ala | Pro | Arg | Gly | Pro | Ala | Arg | Phe | Leu | Pro | Leu | Pro |
| | 370 | | | | | 375 | | | | | 380 | | | | |
| Gly | Leu | Pro | Pro | Ala | Leu | Pro | Glu | Pro | Pro | Gly | Ile | Leu | Ala | Pro | Gln |
| 385 | | | | | 390 | | | | | 395 | | | | | 400 |

-continued

```
Pro Pro Asp Val Gly Ser Ser Asp Pro Leu Arg Leu Val Glu Pro Ser
            405                 410                 415

Gln Leu Xaa Ser Pro Ser Phe Xaa Xaa
            420             425
```

FIBROBLAST GROWTH FACTOR 21 PROTEINS

This present invention relates to fibroblast growth factor 21 (FGF21) proteins, pharmaceutical compositions comprising FGF21 proteins, and methods for treating type 2 diabetes, obesity, dyslipidemia, and/or metabolic syndrome.

FGF21 is a hormone that functions as an important metabolic regulator of glucose and lipid homeostasis. FGF21 promotes glucose uptake in adipocytes by up-regulating GLUT1 expression, a mechanism distinct from that of insulin. In diabetic rodents and monkeys, human FGF21 lowered fasting serum concentrations of glucose, and reduced fasting serum concentrations of triglycerides, insulin and glucagon. Furthermore, in rodent models of diet induced obesity, FGF21 administration led to cumulative body weight loss in a dose dependent manner. Thus, FGF21 has potential utility for the treatment of diabetes, obesity, dyslipidemia, and metabolic syndrome.

FGF21 proteins have been described in WO2010/042747, WO2010/285131, and WO2009/149171.

Problems associated with human wild type FGF21 and known FGF21 proteins are a short half-life in vivo, a low potency and/or pharmaceutical instability of the molecules. Thus, there is still a need for alternative FGF21 proteins that are long-acting, potent and/or stable.

The present invention provides alternative FGF21 proteins. Certain FGF21 proteins of the present invention have advantages over human wild type FGF21 and known FGF21 proteins disclosed in the art. These advantages include having an extended half-life, improved potency and/or improved pharmaceutical stability. In addition to improved potency, certain FGF21 proteins of the present invention have one or more advantageous stability characteristics that are useful for efficient manufacturing and/or formulation as a therapeutic protein, including reduced proteolytic degradation in vivo, reduced susceptibility to oxidation, lowered propensity to aggregate at high concentrations, lowered levels of post-translational modifications and proteolysis during production in mammalian cell systems, and/or improved chemical stability. Additionally, the FGF21 proteins of the present invention are potentially useful for the treatment of type 2 diabetes, obesity, dyslipidemia, and/or metabolic syndrome.

The present invention provides a FGF21 protein, wherein the amino acid sequence consists of a first polypeptide fused to a second polypeptide, wherein the first polypeptide comprises an IgG4 Fc portion, wherein the Fc portion consists of a hinge region, CH2 and CH3 constant region domains of an antibody, the second polypeptide comprises a FGF21 protein having the amino acid sequence of SEQ ID NO: 1, and wherein the C-terminus of the first polypeptide is fused to the N-terminus of the second polypeptide via a linker.

Furthermore, the present invention provides a FGF21 protein, wherein the amino acid sequence consists of a first polypeptide fused to a second polypeptide, wherein the first polypeptide comprises an IgG4 Fc portion having the amino acid sequence of SEQ ID NO: 14, the second polypeptide comprises a FGF21 protein having the amino acid sequence of SEQ ID NO: 1, and wherein the C-terminus of the first polypeptide is fused to the N-terminus of the second polypeptide via a linker.

The present invention also provides a FGF21 protein, wherein the amino acid sequence consists of a first polypeptide fused to a second polypeptide, wherein the first polypeptide comprises an IgG4 Fc portion having the amino acid sequence of SEQ ID NO: 14, the second polypeptide comprises a FGF21 protein having the amino acid sequence of SEQ ID NO: 1, and wherein the C-terminus of the first polypeptide is fused to the N-terminus of the second polypeptide via a linker having the amino acid sequence of SEQ ID NO: 11.

The present invention provides a FGF21 protein, wherein the amino acid sequence is (SEQ ID NO: 5)
ESKYGPPCPPCPAPEAAGGPSVFLFPPKPKDTLMISRTPEVTCVVVDV

SQEDPEVQFNWYVDGVEVHNAKTKPREEQFNSTYRVVSVLTVLHQDWL

NGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRL

TVDKSRWQEGNVFSCSVMHEALHNHYTQKSLSLSLGGGGGSGGGGSGG

GGSAHPIPDSSPLLQFGGQVRQRYLYTDDAQQTECHLEIREDGTVGCA

ADQSPESLLQLKALKPGVIQILGVKTSRFLCQRPDGALYGSLHFDPEA

CSFREDLKEDGYNVYQSEAHGLPLHLPGDKSPHRKPAPRGPARFLPLP

GLPPALPEPPGILAPQPPDVGSSDPLRLVEPSQLRSPSFE.

The FGF21 protein of SEQ ID NO: 5 described above includes the IgG4 Fc portion sequence of SEQ ID NO: 14, the linker sequence of SEQ ID NO: 11 that is identified in bold, and the FGF21 protein of SEQ ID NO: 1 that is underlined.

Furthermore, the present invention provides a FGF21 protein, wherein the amino acid sequence is (SEQ ID NO: 15)
ESKYGPPCPPCPAPEAAGGPSVFLFPPKPKDTLMISRTPEVTCVVVDV

SQEDPEVQFNWYVDGVEVHNAKTKPREEQFNSTYRVVSVLTVLHQDWL

NGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRL

TVDKSRWQEGNVFSCSVMHEALHNHYTQKSLSLSLGGGGGSGGGGSGG

GGSAHPIPDSSPLLQFGGQVRQRYLYTDDAQQTECHLEIREDGTVGCA

ADQSPESLLQLKALKPGVIQILGVKTSRFLCQRPDGALYGSLHFDPEA

CSFREX$_1$LX$_2$EDGYNVYQSEAHGLPLHLPGDKSPHRKPAPRGPARFLPL

PGLPPALPEPPGILAPQPPDVGSSDPLRLVEPSQLX$_3$SPSFX$_4$X$_5$ wherein $X_1$ is L or D, $X_2$ is L or K, $X_3$ is R or L, $X_4$ is L or E, and $X_5$ is G or is absent. The present invention also provides a FGF21 protein of SEQ ID NO: 15, wherein the $X_1$ is D, $X_2$ is L or K, $X_3$ is L, $X_4$ is L, and $X_5$ is G. Furthermore, the present invention provides a FGF21 protein of SEQ ID NO: 15, wherein $X_1$ is L or D, $X_2$ is L or K, $X_3$ is R, $X_4$ is E, and $X_5$ is absent.

The present invention provides a FGF21 protein of SEQ ID NO: 15, wherein the FGF21 protein is selected from the group consisting of SEQ ID NO: 5, SEQ ID NO: 6, SEQ ID NO: 7, SEQ ID NO: 8, and SEQ ID NO: 9. The present invention also provides a FGF21 protein of SEQ ID NO: 15, wherein the FGF21 protein is selected from the group consisting of SEQ ID NO: 8 and SEQ ID NO: 9. Furthermore, the present invention provides a FGF21 protein of SEQ ID NO: 15, wherein the FGF21 protein is selected from the group consisting of SEQ ID NO: 5, SEQ ID NO: 6, and SEQ ID NO: 7. The most preferred FGF21 protein is SEQ ID NO: 5.

The present invention also provides a pharmaceutical composition comprising a FGF21 protein of the present invention and at least one pharmaceutically acceptable carrier, diluent, or excipient.

The present invention also provides a method of treating type 2 diabetes, obesity, dyslipidemia, and/or metabolic syndrome in a patient comprising administering to the patient a FGF21 protein of the present invention.

The present invention also provides a method of treating type 2 diabetes, obesity, dyslipidemia, and/or metabolic syndrome in a patient comprising administering to the patient a pharmaceutical composition of the present invention.

Furthermore, the present invention provides a FGF21 protein of the present invention for use in therapy. Preferably, the present invention provides a FGF21 protein of the present invention for use in the treatment of type 2 diabetes, obesity, dyslipidemia, and/or metabolic syndrome.

Furthermore, the present invention provides the use of a FGF21 protein of the present invention in the manufacture of a medicament for the treatment of type 2 diabetes, obesity, dyslipidemia, and/or metabolic syndrome.

The present invention also relates to polynucleotides encoding the above-described FGF21 protein of the present invention.

Furthermore, the present invention provides a polynucleotide encoding the FGF21 protein of the present invention, wherein the amino acid sequence of the FGF21 protein consists of a first polypeptide fused to a second polypeptide, wherein the first polypeptide comprises an IgG4 Fc portion, wherein the Fc portion consists of a hinge region, CH2 and CH3 constant region domains of an antibody, the second polypeptide comprises a FGF21 protein having the amino acid sequence of SEQ ID NO: 1, and wherein the C-terminus of the first polypeptide is fused to the N-terminus of the second polypeptide via a linker.

The present invention also provides a polynucleotide encoding the FGF21 protein of the present invention, wherein the amino acid sequence of the FGF21 protein consists of a first polypeptide fused to a second polypeptide, wherein the first polypeptide comprises an IgG4 Fc portion having the amino acid sequence of SEQ ID NO: 14, the second polypeptide comprises a FGF21 protein having the amino acid sequence of SEQ ID NO: 1, and wherein the C-terminus of the first polypeptide is fused to the N-terminus of the second polypeptide via a linker.

Furthermore, the present invention provides a polynucleotide encoding the FGF21 protein of the present invention, wherein the amino acid sequence of the FGF21 protein consists of a first polypeptide fused to a second polypeptide, wherein the first polypeptide comprises an IgG4 Fc portion having the amino acid sequence of SEQ ID NO: 14, the second polypeptide comprises a FGF21 protein having the amino acid sequence of SEQ ID NO: 1, and wherein the C-terminus of the first polypeptide is fused to the N-terminus of the second polypeptide via a linker having the amino acid sequence of SEQ ID NO: 11.

Furthermore, the present invention provides a polynucleotide encoding the FGF21 protein of the present invention, wherein the amino acid sequence of the FGF21 protein is

```
                                      (SEQ ID NO: 5)
ESKYGPPCPPCPAPEAAGGPSVFLFPPKPKDTLMISRTPEVTCVVV

DVSQEDPEVQFNWYVDGVEVHNAKTKPREEQFNSTYRVVSVLTVLH

QDWLNGKEYKCKVSNKGLPSSIEKTISKAKGQPREPQVYTLPPSQE

EMTKNQVSLTCLVKGFYPSDIAVEWESNGQPENNYKTTPPVLDSDG

SFFLYSRLTVDKSRWQEGNVFSCSVMHEALHNHYTQKSLSLSLGGG
```

```
                       -continued
GGSGGGGSGGGGSAHPIPDSSPLLQFGGQVRQRYLYTDDAQQTECH

LEIREDGTVGCAADQSPESLLQLKALKPGVIQILGVKTSRFLCQRP

DGALYGSLHFDPEACSFREDLKEDGYNVYQSEAHGLPLHLPGDKSP

HRKPAPRGPARFLPLPGLPPALPEPPGILAPQPPDVGSSDPLRLVE

PSQLRSPSFE.
```

The present invention also provides a polynucleotide encoding the FGF21 protein of the present invention, wherein the nucleotide sequence is SEQ ID NO: 13.

The polynucleotides encoding the above-described proteins may be in the form of RNA or in the form of DNA, which DNA includes cDNA, and synthetic DNA. The DNA may be double-stranded or single-stranded. The coding sequences that encode the proteins of the present invention may vary as a result of the redundancy or degeneracy of the genetic code.

The polynucleotides that encode for the proteins of the present invention may include the following: only the coding sequence for the proteins, the coding sequence for the proteins and additional coding sequence, such as a leader or secretory sequence or a pro-protein sequence; the coding sequence for the proteins and non-coding sequence, such as introns or non-coding sequence 5' and/or 3' of the coding sequence for the proteins. Thus the term "polynucleotide encoding a protein" encompasses a polynucleotide that may include not only coding sequence for the proteins but also a polynucleotide that includes additional coding and/or non-coding sequence, such as SEQ ID NO: 13.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The FGF21 proteins of the present invention may readily be produced in mammalian cells such as CHO, NS0, HEK293 or COS cells; in bacterial cells such as *E. coli, Bacillus subtilis*, or *Pseudomonas fluorescence*; or in fungal or yeast cells. The host cells are cultured using techniques well known in the art. The preferred mammalian host cell is the CHOK1SV cell line containing a glutamine synthetase (GS) expression system (see U.S. Pat. No. 5,122,464).

The vectors containing the polynucleotide sequences of interest (e.g., the proteins of FGF21 and expression control sequences) can be transferred into the host cell by well-known methods, which vary depending on the type of cellular host. For example, calcium chloride transformation is commonly utilized for prokaryotic cells, whereas calcium phosphate treatment or electroporation may be used for other cellular hosts.

Various methods of protein purification may be employed and such methods are known in the art and described, for example, in Deutscher, *Methods in Enzymology* 182: 83-89 (1990) and Scopes, *Protein Purification: Principles and Practice,* 3rd Edition, Springer, N.Y. (1994).

The present invention also provides a process for producing a homodimer wherein the amino acid sequence of each polypeptide of said homodimer is SEQ ID NO: 5, said process comprising the steps of:
  i) cultivating a mammalian host cell comprising a polynucleotide encoding the polypeptide having the amino acid sequence of SEQ ID NO: 5 under conditions such that said polypeptide sequence is expressed; and ii) recovering from said host cell a homodimer wherein the amino acid sequence of each polypeptide of said homodimer is SEQ ID NO: 5.

The FGF21 protein of the present invention is a homodimer when expressed in mammalian cells. "Homodimer" as used herein, refers to two FGF21 proteins of the present invention having the same amino acid sequence (for example SEQ ID NO: 5) that associate through non-covalent interactions and intermolecular disulfide bonds in the Fc portion.

The present invention provides a homodimer of a FGF21 protein, wherein the amino acid sequence consists of a first polypeptide fused to a second polypeptide, wherein the first polypeptide comprises an IgG4 Fc portion, wherein the Fc portion consists of a hinge region, CH2 and CH3 constant region domains of an antibody, the second polypeptide comprises a FGF21 protein having the amino acid sequence of SEQ ID NO: 1, and wherein the C-terminus of the first polypeptide is fused to the N-terminus of the second polypeptide via a linker.

Furthermore, the present invention provides a homodimer of a FGF21 protein, wherein the amino acid sequence consists of a first polypeptide fused to a second polypeptide, wherein the first polypeptide comprises an IgG4 Fc portion having the amino acid sequence of SEQ ID NO: 14, the second polypeptide comprises a FGF21 protein having the amino acid sequence of SEQ ID NO: 1, and wherein the C-terminus of the first polypeptide is fused to the N-terminus of the second polypeptide via a linker.

The present invention also provides a homodimer of a FGF21 protein, wherein the amino acid sequence consists of a first polypeptide fused to a second polypeptide, wherein the first polypeptide comprises an IgG4 Fc portion having the amino acid sequence of SEQ ID NO: 14, the second polypeptide comprises a FGF21 protein having the amino acid sequence of SEQ ID NO: 1, and wherein the C-terminus of the first polypeptide is fused to the N-terminus of the second polypeptide via a linker having the amino acid sequence of SEQ ID NO: 11.

The present invention provides a homodimer of a FGF21 protein, wherein the amino acid sequence is (SEQ ID NO: 5)
ESKYGPPCPPCPAPEAAGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGGGGSGGGGSGGGGSAH

PIPDSSPLLQFGGQVRQRYLYTDDAQQTECHLEIREDGTVGCAADQSPE

SLLQLKALKPGVIQILGVKTSRFLCQRPDGALYGSLHFDPEACSFREDL

KEDGYNVYQSEAHGLPLHLPGDKSPHRKPAPRGPARFLPLPGLPPALPE

PPGILAPQPPDVGSSDPLRLVEPSQLRSPSFE.

The FGF21 protein of SEQ ID NO: 5 described above includes the IgG4 Fc portion sequence of SEQ ID NO: 14, the linker sequence of SEQ ID NO: 11 that is identified in bold, and the FGF21 protein of SEQ ID NO: 1 that is underlined.

Furthermore, the present invention provides a homodimer of a FGF21 protein, wherein the amino acid sequence is (SEQ ID NO: 15)
ESKYGPPCPPCPAPEAAGGPSVFLFPPKPKDTLMISRTPEVTCVVVDV

SQEDPEVQFNWYVDGVEVHNAKTKPREEQFNSTYRVVSVLTVLHQDWL

NGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRL

TVDKSRWQEGNVFSCSVMHEALHNHYTQKSLSLSLGGGGGSGGGGSGG

GGSAHPIPDSSPLLQFGGQVRQRYLYTDDAQQTECHLEIREDGTVGCA

ADQSPESLLQLKALKPGVIQILGVKTSRFLCQRPDGALYGSLHFDPEA

CSFREX$_1$LX$_2$EDGYNVYQSEAHGLPLHLPGDKSPHRKPAPRGPARFLPL

PGLPPALPEPPGILAPQPPDVGSSDPLRLVEPSQLX$_3$SPSFX$_4$X$_5$ wherein $X_1$ is L or D, $X_2$ is L or K, $X_3$ is R or L, $X_4$ is L or E, and $X_5$ is G or is absent. The present invention also provides a homodimer of a FGF21 protein of SEQ ID NO: 15, wherein the $X_1$ is D, $X_2$ is L or K, $X_3$ is L, $X_4$ is L, and $X_5$ is G. Furthermore, the present invention provides a homodimer of a FGF21 protein of SEQ ID NO: 15, wherein $X_1$ is L or D, $X_2$ is L or K, $X_3$ is R, $X_4$ is E, and $X_5$ is absent.

The present invention provides a homodimer of a FGF21 protein of SEQ ID NO: 15, wherein the FGF21 protein is selected from the group consisting of SEQ ID NO: 5, SEQ ID NO: 6, SEQ ID NO: 7, SEQ ID NO: 8, and SEQ ID NO: 9. The present invention also provides a homodimer of a FGF21 protein of SEQ ID NO: 15, wherein the FGF21 protein is selected from the group consisting of SEQ ID NO: 8 and SEQ ID NO: 9. Furthermore, the present invention provides a homodimer of a FGF21 protein of SEQ ID NO: 15, wherein the FGF21 protein is selected from the group consisting of SEQ ID NO: 5, SEQ ID NO: 6, and SEQ ID NO: 7. The most preferred FGF21 protein is SEQ ID NO: 5.

The present invention also relates to polynucleotides encoding the above-described homodimer of a FGF21 protein of the present invention.

The present invention also provides a pharmaceutical composition comprising a homodimer of a FGF21 protein of the present invention and at least one pharmaceutically acceptable carrier, diluent, or excipient.

The present invention also provides a method of treating type 2 diabetes, obesity, dyslipidemia, and/or metabolic syndrome in a patient comprising administering to the patient a homodimer of a FGF21 protein of the present invention.

Furthermore, the present invention provides a homodimer of a FGF21 protein of the present invention for use in therapy. Preferably, the present invention provides a homodimer of a FGF21 protein of the present invention for use in the treatment of type 2 diabetes, obesity, dyslipidemia, and/or metabolic syndrome.

Furthermore, the present invention provides the use of a homodimer of a FGF21 protein of the present invention in the manufacture of a medicament for the treatment of type 2 diabetes, obesity, dyslipidemia, and/or metabolic syndrome.

The FGF21 proteins of the present invention may be glycosylated in the Fc portion at a highly conserved N-glycosylation site. Furthermore, the FGF21 proteins of the present invention are a homodimer when expressed in mammalian cells. "Homodimer" as used herein, refers to two FGF21 proteins of the present invention having the same amino acid sequence, for example SEQ ID NO: 5, that associate through non-covalent interactions and intermolecular disulfide bonds in the Fc portion.

Full length human wild type FGF21 is a 208 amino acid polypeptide containing a 27 amino acid signal peptide. Mature human wild type FGF21 comprises the full length polypeptide without the 27 amino acid signal peptide, resulting in a 181 amino acid polypeptide (SEQ ID NO: 2).

The changes in amino acid positions of the FGF21 proteins of the present invention are determined from the amino acid positions in the polypeptide of mature human wild type FGF21 (SEQ ID NO: 2) without an IgG4 Fc portion and a linker. For example, the IgG4 Fc portion of the FGF21 protein of SEQ ID NO: 5 includes amino acids 1 through 228, the linker of the FGF21 protein of SEQ ID NO: 5 includes amino acids 229 through 244, and the FGF21 protein of the FGF21 protein of SEQ ID NO: 5 includes amino acids 245 through 424. Thus, a substitution described herein as "A31C" refers to substitution of the amino acid Cys for the wild type amino acid Ala at position 31 of the mature human wild type FGF21.

It is important to note that a substitution of one amino acid residue in a particular protein may affect the characteristics of the proteins as a whole, and that overall effect may be beneficial or detrimental to the pharmacological potency and/or pharmaceutical stability. For example, one amino acid substitution, P115W, increases the potency of the FGF21 protein; however, P115W is also believed to contribute to the self-association that causes aggregation. Therefore, the overall effect is detrimental to the proteins, and thus the substitution P115W is not included in the FGF21 proteins of the present invention. Another example relates the amino acid substitution R175L, which increases the potency of the FGF21 protein. However, FGF21 proteins having the R175L substitution were found susceptible to proteolysis, thus the overall effect was detrimental. To address the C-terminal proteolysis observed with the FGF21 proteins of the present invention, amino acids at positions 180 and 181 (L at position 180 and G at position 181) are substituted with the amino acid E at position 180 and the amino acid at 181 is deleted. These modifications substantially decrease C-terminal proteolysis, but also reduce the pharmacological potency of the FGF21 protein by 25-fold measured in the human 293 cell-βKlotho-SRE luc assay. Surprisingly, potency is restored by reverting the amino acid residue at position 175 (R175L) back to the wild-type R. Therefore, the overall effect of this substitution (R175L) is detrimental to the proteins, and thus the substitution R175L is not included in the preferred FGF21 proteins of the present invention.

Certain FGF21 proteins of the present invention are potent, biologically active proteins as demonstrated for SEQ ID NO:5 in Examples 2 and 3. The preferred FGF21 proteins of the present invention contain amino acid substitutions that together not only improve potency, but also are compatible with other amino acid changes that, in turn, may provide for improved stability characteristics and increased in vivo stability. The amino acid substitutions in the preferred FGF21 proteins of the present invention that improve potency include D127K, S167R, and G174L (see Examples 2 and 3).

Exposure of a concentrated protein solution of human wild type FGF21 to a pharmaceutical preservative, such as m-cresol, increases the propensity of the protein to form aggregates. Structural stabilization through the introduction of an additional disulfide bond improves the preservative compatibility as well as the thermal stability of human wild type FGF21. The FGF21 proteins of the present invention incorporate the amino acid substitutions A31C and G43C that greatly improve thermal stability and preservative compatibility without compromising biological activity. High potency FGF21 proteins that also include the A31C/G43C substitutions have been described previously. Those reported proteins display significantly improved preservative compatibility relative to wild type FGF21, but they are still prone to aggregation in the presence of preservative. This protein aggregation increases the risk of immunogenicity, thereby reducing the acceptability of the proteins as a therapeutic protein.

Fusion of FGF21 proteins to the Fc portion also makes self-association more prominent. This behavior may be due to the homodimeric structure of the Fc fusions that could lead to avidity, stabilizing self interaction and aggregation.

The preferred proteins of the present invention include the amino acid substitutions L98D and L100K, which surprisingly result in significantly lower high molecular weight aggregate formation at high concentrations. Advantageously, the amino acid substitutions L98D and L100K do not decrease the potency of the proteins, but they do minimize the detrimental aggregation problem.

A preferred commercial expression system for manufacture of the FGF21 proteins of the present invention is the mammalian CHO-K1 cell line. However, the mammalian cell lines CHO-K1 and HEK293 may cause post-translational modifications to mature human wild type FGF21 through sulfation of the tyrosine side chain at position 179. Sulfation of tyrosine residues at positions 179 and 180 (if present) decreases potency and is an undesirable source of product heterogeneity. Thus, when an FGF21 protein having Tyr at position 179 and/or 180 is expressed from CHO-K1 or HEK293 cell lines, some proportion of the expressed proteins may be sulfated at position 179, others may be sulfated at position 180, while others may be sulfated at both positions and some at neither position. This leads to a heterogeneous and unpredictable protein population with decreased potency.

The preferred FGF21 proteins of the present invention include an amino acid substitution that has resolved this detrimental sulfation. Thus, the amino acid substitution Y179F has been incorporated into the proteins. Y179F eliminates the sulfation resulting from production in CHO-K1 and HEK293 cells. Moreover, the amino acid substitution Y179F is compatible with the other favored amino acid substitutions of the present invention, and is determined to be a neutral change with regard to potency.

Human wild type FGF21 is susceptible to proteolytic degradation in vivo. A major proteolytic fragment recovered from sera after intravenous or subcutaneous injection of mice or cynomolgus monkeys with wild type FGF21 is the fragment that terminates at position 171. The FGF21 fragment spanning residues 1 to 171 has been determined to be ~100-fold less potent in in vitro potency assays. Thus, eliminating this proteolytic cleavage site may improve drug efficacy by increasing exposure to active drug. The amino acid substitution G170E has been shown to significantly slow cleavage in mouse and virtually eliminate proteolysis at the 171 position when measured after 24 hours in cynomolgus monkeys. The G170E substitution does not impact potency and is compatible with the desired physicochemical stability profile. Therefore, the amino acid substitution G170E is incorporated into the FGF21 proteins of the present invention.

Human wild type FGF21 is also susceptible to a carboxypeptidase produced in CHO-K1 manufacture, and the amino acid substitution A180E and amino acid deletion at position 181 slows this processing, thereby reducing heterogeneity of the length of the protein expressed (i.e., heterogeneity in the number of amino acid residues in the mature protein expressed by the cell line). Although the amino acid substitution A180E and the amino acid deletion at position 181 do not eliminate C-terminal proteolysis in mammalian cell expression, it is quite effective at slowing proteolysis while maintaining potency in the context of other desired amino acid substitutions found in the FGF21 proteins of the present invention. In view of this advantageous characteristic, the amino acid substitution A180E and the amino acid deletion at position 181 are incorporated into the preferred FGF21 proteins of the present invention.

The FGF21 proteins of the present invention are fused via a linker to the Fc portion of an immunoglobulin. The Fc portion used for the FGF21 proteins of the present invention is derived from an IgG4 Fc portion. It is even more preferable that the FGF21 proteins of the present invention contain an Fc portion which is derived from human IgG4, but comprises one or more substitutions compared to the wild type human sequence. As used herein, the Fc portion of an immunoglobulin has the meaning commonly given to the term in the field of immunology. Specifically, this term refers to an antibody fragment which does not contain the two antigen binding regions (the Fab fragments) from the antibody. The Fc portion consists of a hinge region, CH2 and CH3 constant region domains of an antibody.

It is well known in the art that mammalian expression of antibodies results in glycosylation. Typically, glycosylation occurs in the Fc portion of the antibody at a highly conserved N-glycosylation site. N-glycans typically attach to asparagine.

Thus, the FGF21 proteins of the present invention are derived from the human IgG4 Fc region of an immunoglobulin fused to a FGF21 protein of the present invention. Preferably, the Fc portion of the FGF21 protein comprises the sequence of SEQ ID NO: 14:

```
                                          (SEQ ID NO: 14)
ESKYGPPCPPCPAPEAAGGPSVFLEPPKPKDTLMISRTPEVTCVVVD

VSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMT

KNQVSLTCLVKGFYPSDIAVEWESNGQPENNYKTTPPVLDSDGSFFL

YSRLTVDKSRWQEGNVFSCSVMHEALHNHYTQKSLSLSLG
```

The N-terminal amino acid of a FGF21 protein of the present invention is fused to the C-terminus of each heavy chain of the Fc portion via a glycine-rich linker (G-rich), designated by L, with the number immediately preceding the L referring to the number of repeating linker units separating the FGF21 protein from the Fc portion. A linker unit is defined as a Gly-Gly-Gly-Gly-Ser sequence (SEQ ID NO: 10). The linker optionally contains an Ala linked to the final Ser if multiple linker repeats are used.

Fc portion of the FGF21 proteins of the present invention are preferably fused together via 1, 2, or 3 repeats of the G-rich peptide linker, -Gly-Gly-Gly-Gly-Ser- (SEQ ID NO: 10), designated as 1L. Additional G-rich linkers of the present invention comprise the sequences -Gly-Gly-Gly-Gly-Ser-Gly-Gly-Gly-Gly-Ser-Ala (SEQ ID NO: 12), designated 2L and -Gly-Gly-Gly-Gly-Ser-Gly-Gly-Gly-Gly-Ser-Gly-Gly-Gly-Gly-Ser-Ala (SEQ ID NO: 11), designated 3L. The most preferred glycine-rich linker of the present invention is linker 3L, -Gly-Gly-Gly-Gly-Ser-Gly-Gly-Gly-Gly-Ser-Gly-Gly-Gly-Gly-Ser-Ala (SEQ ID NO: 11).

It is understood that the IgG4 Fc is comprised of the constant region from both heavy chains of an IgG4 antibody. Thus, the FGF21 proteins of the present invention are comprised of an IgG4 Fc portion fused with two FGF21 proteins having the same amino acid sequence via G-rich linkers to each C-terminus of each IgG4 Fc portion polypeptide.

The pharmaceutical compositions of the FGF21 proteins of the present invention may be administered by any means known in the art that achieve the generally intended purpose to treat type 2 diabetes, obesity, dyslipidemia, and/or metabolic syndrome. The preferred route of administration is parenteral. The dosage administered will be dependent upon the age, health, and weight of the recipient, kind of concurrent treatment, if any, frequency of treatment, and the nature of the effect desired. Typical dosage levels can be optimized using standard clinical techniques and will be dependent on the mode of administration and the condition of the patient and can be determined by a person having ordinary skill in the art.

The FGF21 proteins of the present invention are formulated according to known methods to prepare pharmaceutically useful compositions. A desired formulation is a stable lyophilized product that is reconstituted with an appropriate diluent or an aqueous solution of high purity with optional pharmaceutically acceptable carriers, preservatives, excipients or stabilizers [*Remington, The Science and Practice of Pharmacy*, 19th edition, Gennaro, ed., Mack Publishing Co., Easton, Pa. 1995].

The FGF21 proteins of the present invention may be formulated with a pharmaceutically acceptable buffer, and the pH adjusted to provide acceptable stability, and a pH acceptable for administration. Moreover, the FGF21 compositions of the present invention may be placed into a container such as a vial, a cartridge, a pen delivery device, a syringe, intravenous administration tubing or an intravenous administration bag.

The term "dyslipidemia" means a disorder of lipoprotein metabolism, including lipoprotein overproduction or deficiency. Dyslipidemia may be manifested by elevation of the total cholesterol, low-density lipoprotein (LDL) cholesterol and the triglyceride concentrations, and/or a decrease in high-density lipoprotein (HDL) cholesterol concentration in the blood.

The term "metabolic syndrome" is characterized by a group of metabolic risk factors in one person. They include: abdominal fat—in most men, a 40-inch waist or greater; high blood sugar—at least 110 milligrams per deciliter (mg/dl) after fasting; high triglycerides—at least 150 mg/dL in the bloodstream; low HDL—less than 40 mg/dl; and/or, blood pressure of 130/85 or higher.

The term "obesity" is defined as a condition in which there is an excess of subcutaneous fat in proportion to lean body mass (Stedman's Medical Dictionary 28th edition, 2006, Lippincott Williams & Wilkins).

A "patient" is a mammal, preferably a human.

The term "treating" (or "treat" or "treatment") means slowing, reducing, or reversing the progression or severity of an existing symptom, disorder, condition, or disease.

The term "therapeutically effective amount" refers to the amount or dose of a protein of the present invention, which, upon single or multiple dose administration to a patient, provides the desired treatment.

The term "type 2 diabetes" is characterized by excess glucose production in spite of the availability of insulin, and circulating glucose levels remain excessively high as a result of inadequate glucose clearance.

The present invention may be practiced by referencing the following examples. However, this is not to be interpreted as limiting the scope of the present invention. Furthermore, the FGF21 proteins of the present invention described and exemplified in the examples are expressed in mammalian cells, and therefore are a homodimer.

EXAMPLE 1

Expression of FGF21 proteins in CHOK1SV Cells

The FGF21 proteins of the present invention are produced in a mammalian cell expression system using CHOK1SV cells. Genes coding for the FGF21 proteins of the present invention are sub-cloned into the Glutamine Synthetase (GS)-containing expression plasmid backbones (pEE12.4-based plasmids). The cDNA sequence encoding the FGF21 proteins of the present invention is fused in frame with the coding sequence of preferred signal peptide sequences to enhance secretion of the desired product into the tissue culture medium. The preferred signal peptide sequences are the polypeptides as shown in the amino acid sequences SEQ ID NO: 3 and SEQ ID NO: 4.

The expression is driven by the viral cytomegalovirus (CMV) promoter. CHOK1SV cells are stably transfected using electroporation and the appropriate amount of recombinant expression plasmid, and the transfected cells are maintained in suspension culture, at the adequate cell density. Selection of the transfected cells is accomplished by growth in methionine sulfoximine (MSX)-containing serum-free medium and incubated at 35-37° C. and 5-7% $CO_2$.

Clonally-derived cell lines are measured or determined by use of a flow cytometer. The expression of a FGF21 protein in mammalian cells generally yields the natural N-terminal sequence, ESKY, i.e. without a methionine residue at the N-terminus, such as the FGF21 protein shown by the amino acid sequence of SEQ ID NO: 5.

FGF21 proteins secreted into the media from the CHO cells may be purified by Protein A affinity chromatography followed by preparative size exclusion chromatography following standard chromatographic techniques. Briefly, FGF21 proteins from harvested media are captured onto Mab Select Protein A (GE, Piscataway, N.J.) with PBS pH 7.4 running buffer; briefly washed with running buffer to remove non-specifically bound material; and eluted with 10 mM citrate pH 3.0. Fractions containing FGF21 proteins are pooled and pH is neutralized by adding ⅒ volume of 1M Tris pH 8.0. The neutralized pool is concentrated and loaded onto a Superdex 200 size exclusion chromatography column (GE, Piscataway, N.J.) with PBS pH 7.4 mobile phase. Fractions containing monomeric FGF21 protein (a covalently linked homodimer) are pooled, concentrated, and stored.

Alternatively, the cell free media containing FGF21 proteins may be heated to 50-60° C. for up to two hours, cooled, treated with detergent (Triton X-100) for viral inactivation, applied to a Mab Select Protein A (GE Healthcare) column, and washed successively with pH 7 Tris buffered solution with and without sodium chloride to remove non-specifically bound materials. The FGF21 protein is eluted from the column using 20 mM citrate pH 3 and held at pH 3.4 to 3.7 for up to two hours for viral inactivation. The solution is adjusted to pH 4.8 to 5.2 by addition of Tris buffer and sodium chloride and mixed for at least 15 minutes. Precipitates that form are removed by depth filtration (Millipore). The FGF21 protein is further purified by cation exchange chromatography using resins such as Poros HS 50 (Life Technologies) or SP Sepharose HP (GE Healthcare). The cation exchange column is eluted with sodium chloride in a pH 5 sodium acetate buffered solution. The FGF protein may be further purified by hydrophobic interaction chromatography on Phenyl Sepharose HP (GE Healthcare) by adjusting the pH from 7 to 8 using a Tris buffer, addition of sodium sulfate and application to the column followed by elution with a reversed concentration gradient of sodium sulfate. Purified FGF21 protein can be passed through a viral retention filter such as Planova 20N (Asahi Kasei Medical) followed by concentration/diafiltration into 10 mM citrate, 150 mM NaCl pH 7 using tangential flow ultrafiltration on a regenerated cellulose membrane (Millipore).

EXAMPLE 2

3T3-L1-βKlotho Fibroblast Glucose Uptake Assay

3T3-L1-βKlotho fibroblasts are generated from 3T3-L1 fibroblasts by retroviral transduction of a CMV-driven mammalian expression vector containing the coding sequence of wild type mouse βKlotho and a blasticidin resistance marker. Blasticidin-resistant cells are selected after growth for 14 days in the presence of 15 µM blasticidin, and βKlotho protein expression is verified by immunoblot with an anti-βKlotho antibody. The 3T3-L1-βKlotho fibroblasts are maintained in Dulbecco's Modified Eagle Medium (DMEM) with 10% calf serum, and 15 µM blasticidin until plated for experimental use.

For glucose uptake, 3T3-L1-βKlotho fibroblasts are plated at 20,000 cells/well in 96-well plates and incubated for 48 hours in DMEM with 10% calf serum. The cells are incubated for 3 hours in DMEM with 0.1% bovine serum albumin (BSA) with or without an FGF21 protein of interest, followed by 1 hour incubation in Krebs-Ringer phosphate (KRP) buffer (15 mM Hepes, pH 7.4, 118 mM NaCl, 4.8 mM KCl, 1.2 mM $MgSO_4$, 1.3 mM $CaCl_2$, 1.2 mM $KH_2PO_4$, 0.1% BSA) containing 100 µM 2-deoxy-D-($^{14}C$) glucose with or without an FGF21 protein. Non-specific binding is determined by incubation of select wells in Krebs-Ringer bicarbonate/Hepes (KRBH) buffer containing 1 mM 2-deoxy-D-($^{14}C$) glucose. The reaction is terminated by addition of 20 µM cytochalasin B to the cells and glucose uptake is measured using a liquid scintillation counter.

Following the protocol essentially as described above, the in vitro potency ($EC_{50}$) of the homodimer of the FGF21 protein of SEQ ID NO: 5 in the 3T3-L1-βKlotho fibroblast glucose uptake assay is determined to be 0.070 nM.

EXAMPLE 3

Human 293 cell-βKlotho-SRE luc Assay

Construction of 293-βKlotho-SRE luc Reporter Cells:

HEK-293 cells (human embryonic kidney cells) are cultured at 37° C., 5% $CO_2$ in growth medium (GM) containing 10% fetal bovine serum (FBS) in Dulbecco's modified Eagle's medium. Cells are cotransfected with a plasmid containing a CMV promoter driven human βKlotho expression cassette and a plasmid containing a Serum Response Element (SRE) driven luciferase expression cassette. The βKlotho expression plasmid also contains an SV40 promoter driven neomycin phosphotransferase expression cassette to confer resistance to the aminoglycoside antibiotic G418. Transfected HEK-293 cells are selected with 600 µg/mL of G418 to select for cells where the transfected plasmids have been integrated into the genome. Selected cells are cloned by dilution and tested for an increase in luciferase production at 24 hours post addition of FGF21. The clone demonstrating the largest FGF21 dependant increase in luciferase is chosen as the cell line used to measure relative FGF21 proteins activity.
293-βKlotho-SRE luc FGF21 Activity Assay:

293-βKlotho-SRE luc cells are rinsed and placed into CD 293 suspension culture media (Invitrogen). Cells are grown in suspension overnight at 37° C., 6% $CO_2$, 125 rpm. Cells are counted, pelleted by centrifugation, and re-suspended in CD 293 media containing 0.1% BSA. Cells are placed in white 96 well plates at 25,000 cells per well. A four-fold serial dilution in CD 293/0.1% BSA is prepared for each FGF21 protein to generate eight dilutions with final concentrations from 100 nM to 0.006 nM. Dilutions are added to cells in triplicate and incubated for 16-20 hours at 37° C., 5% $CO_2$. Luciferase level is determined by the addition of an equal volume of One-Glo™ luciferase substrate (Promega) and measuring relative luminescence. Data is analyzed using a four parameter logistic model (XLfit version 5.1) to fit the curves and determine $EC_{50}$.

Following the protocol essentially as described above, the average in vitro potency ($EC_{50}$) of the homodimer of the FGF21 protein of SEQ ID NO: 5 in the human 293 cell-βKlotho-SRE luc assay is determined to be 0.51 nM.

EXAMPLE 4

Physical Stability

R175 and E180 Expression Heterogeneity

Production of a homogeneous protein product is desirable since it better ensures a consistent and well-characterized product. To assess product heterogeneity, a 10 μL aliquot of a sample is mixed with 90 μL of DPBS. The sample is analyzed by liquid chromatography-mass spectrometry (LC-MS), using the following conditions: the mobile phase A is 0.05% TFA, the mobile phase B is 0.04% TFA in acetonitrile, the column is a PLRPS 2.1×50 mm column, the injection volume is 15 μL.

TABLE 1

Gradient Conditions for Liquid Chromatographic Separation

| Time (min) | 0 | 1 | 15 | 16 | 20 | 20.1 | 30 |
|---|---|---|---|---|---|---|---|
| % B | 5 | 35 | 40 | 90 | 90 | 5 | 5 |
| Flow (μL/min) | 200 | 200 | 200 | 200 | 200 | 200 | 200 |

A Waters Micromass LCT Premier™ mass spectrometer is set up to a mass range between 400 to 1990 amu, polarity ES+, capillary 3000, sample cone 40 V, aperture 1 is 25 V, the source temperature is 105° C., cone gas flow is 50 L/hour, desolvation temperature is 150° C., and the desolvation gas flow is 600 L/hour.

TABLE 2

LC/MS Characterization of FGF21 Proteins

| | Product | | | | |
|---|---|---|---|---|---|
| FGF21 Protein | 1-425 | 1-424 | 1-422 | 1-411 | 1-379 |
| Homodimer of the FGF21 protein of SEQ ID NO: 8 | | 81.8% | 11.8% | 6.4% | |
| Homodimer of the FGF21 protein of SEQ ID NO: 9 | 48.8% | 49.8% | | 1.2% | 0.1% |
| Homodimer of the FGF21 protein of SEQ ID NO: 5 | | 100% | | | |

Table 2 reports the resulting heterogeneity in each FGF21 protein as determined by LC/MS method. The product 1-425 represents the full length FGF21 protein containing the IgG4 Fc portion, linker and FGF21 protein for the FGF21 protein of SEQ ID NO: 8 and the FGF21 protein of SEQ ID NO: 9. The FGF21 protein of SEQ ID NO: 8 and the FGF21 protein of SEQ ID NO: 9 differ only at position 100 with the FGF21 protein of SEQ ID NO: 8 containing the wild type residue leucine and the FGF21 protein of SEQ ID NO: 9 containing the amino acid residue lysine (L100K) and both proteins have identical C-termini. Both of these proteins are susceptible to C-terminal truncations, especially removal of the amino acid residue glycine at position 181. As shown in Table 2, less than 50% of the purified product for the homodimer of the FGF21 protein of SEQ ID NO: 8 and the homodimer of the FGF21 protein of SEQ ID NO: 9 is the intended full-length 1-425; the 1-424 fragment makes up the largest portion of the purified product. In addition, minor amounts of products 1-422, 1-411, and 1-379 are also detected.

The FGF21 protein of SEQ ID NO: 5 has the amino acid residue at 181 deleted in the genetic construct and amino acid residue 180 has been substituted to glutamic acid (E). These changes protect the C-terminus from degradation during CHO expression, resulting in 100% homogeneous purified 1-424 product.

EXAMPLE 5

Physical Stability

Self-Association at High Concentration

Protein aggregation and self-association is undesired since it could potentially exacerbate unwanted effects such as triggering an immune response. Thus, maintaining the protein in a monomeric state (a covalently linked homodimer) is preferred. To test for the propensity of FGF21 proteins to self-associate, proteins were dialyzed into the buffers listed in Table 3 and analyzed by size exclusion chromatography (SEC) to determine the % high molecular weight (% HMW) of a 1.0 mg/mL solution. % HMW is an indicator of protein aggregation and self-association.

The SEC separation method is performed on a Tosoh Bioscience 3000SWXL, 5 micron column with dimensions 30 cm×0.78 cm. Mobile phase is 0.05 M sodium phosphate, 175 mM NaCl, pH 7 at a flow rate of 0.5 mL/minute. 1.0 mg/mL samples are applied as 10 mcL injections and monitored at an absorbance wavelength of 214 nm, whereas 75 mg/mL samples are applied as 1 mcL injections and monitored at 280 nm.

TABLE 3

Self-Association

| Buffer Composition | 10 mM Citrate, 150 mM NaCl | 10 mM Citrate, 50 mM NaCl | PBS |
|---|---|---|---|
| Homodimer of the FGF21 protein of SEQ ID NO: 8 | | | |
| HMW (%) 1 mg/mL | 4.4% | 4.4% | 4.2% |
| HMW (%) 75 mg/mL | 13.7% | 21.9% | 14.6% |
| Homodimer of the FGF21 protein of SEQ ID NO: 9 | | | |
| HMW (%) 1 mg/mL | 0.7% | 0.8% | 0.8% |
| HMW (%) 75 mg/mL | 2.2% | 3.5% | 2.2% |
| Homodimer of the FGF21 protein of SEQ ID NO: 5 | | | |
| HMW (%) 1 mg/mL | 0.4% | 0.4% | 0.4% |
| HMW (%) 75 mg/mL | 2.0% | 3.6% | 2.2% |

Table 3 illustrates 4-5% HMW for the homodimer of the FGF21 protein of SEQ ID NO: 8 and <1% HMW for the homodimer of the FGF21 protein of SEQ ID NO: 9 and the homodimer of the FGF21 protein of SEQ ID NO: 5 at 1.0 mg/mL for all buffer compositions. Samples were then concentrated to 75 mg/mL to simulate a high concentration formulation and analyzed again by SEC to determine the % HMW. The homodimer of the FGF21 protein of SEQ ID NO: 8 variant contained 13.7-21.9% HMW at 75 mg/mL, whereas the homodimer of the FGF21 protein of SEQ ID NO: 9 contained only 2.2-3.5%. Since the only difference between the FGF21 protein of SEQ ID NO: 8 and the FGF21 protein of SEQ ID NO: 9 is a substitution at position 100 (L100L versus L100K), this data demonstrates that L100K reduces HMW formation.

The FGF21 protein of SEQ ID NO: 5 also contains L100K in addition to other changes, and the lower % HMW is also observed in this homodimer protein.

EXAMPLE 6

Physical Stability

L100K Substitution and % High Molecular Weight

Physical stability of FGF21 proteins is determined as follows. Proteins are dialyzed and prepared at 1-2 mg/mL in 10 mM Citrate pH7, 150 mM NaCl and analyzed by SEC to determine the % HMW (Table 3: "Initial").

The SEC separation method is performed on a Tosoh Bioscience 3000SWXL, 5 micron column with dimensions 30 cm×0.78 cm. Mobile phase is 0.05 M sodium phosphate, 175 mM NaCl, pH 7 at a flow rate of 0.5 mL/minute. Initial low concentration samples are applied as 10 mcL injections and monitored at an absorbance wavelength of 214 nm, whereas the 50 mg/mL samples are applied as 1 mcL injections and monitored at 280 nm.

Next, proteins are concentrated to 50 mg/mL and analyzed again (t=0). The % HMW for the homodimer of the FGF21 protein of SEQ ID NO: 8 increased from 4.5% to 9.3% upon concentration. The % HMW for the homodimer of the FGF21 protein of SEQ ID NO: 9 increased from 0.9% to 1.4% upon concentration. The % HMW for the homodimer of the FGF21 protein of SEQ ID NO: 5 increased from 0.4% to 1.4% upon concentration. Thus, both the homodimer of the FGF21 protein of SEQ ID NO: 9 and the homodimer of the FGF21 protein of SEQ ID NO:5 have lower initial % HMW and lower % HMW when proteins are formulated at 50 mg/mL than the homodimer of the FGF21 protein of SEQ ID NO: 8. These data demonstrate the importance of the L100K mutation that is present in the FGF21 protein of SEQ ID NO:9 and the FGF21 protein of SEQ ID NO: 5, but not present in the FGF21 protein of SEQ ID NO: 8.

The 50 mg/mL formulations are incubated for 4 weeks at 4° C., 25° C., and 40° C. to assess longer-term stability under stress conditions. As shown in Table 4, the % HMW is determined again at 4 weeks time (t=4 weeks). The % HMW for the homodimer of the FGF21 protein of SEQ ID NO: 8 increased from 9.3% to 16.0% at 40° C. The % HMW for the homodimer of the FGF21 protein of SEQ ID NO: 9 increased from 1.4% to 5.5% at 40° C. The % HMW for the homodimer of the FGF21 protein of SEQ ID NO: 5 increased from 0.4% to 5.4% at 40° C. After 4 weeks at 25° C., levels of % HMW were only 3.3% for the homodimer of the FGF21 protein of SEQ ID NO: 9 and the homodimer of the FGF21 protein of SEQ ID NO: 5, whereas they were 13.8% for the homodimer of the FGF21 protein of SEQ ID NO: 8. These data demonstrate the beneficial impact of including the L100K mutation present in the FGF21 protein of SEQ ID NO: 9 and FGF21 protein of SEQ ID NO: 5.

TABLE 4

| | % High Molecular Weight | | |
|---|---|---|---|
| | Initial | 50 mg/mL % HMW (t = 0) | 50 mg/mL % HMW (t = 4 weeks) |
| Homodimer of the FGF21 protein of SEQ ID NO: 8 | | | |
| 10 mM Citrate pH7, 150 mM NaCl | 4.5% | 9.3% | |
| 4° C. | | | 12.1% |
| 25° C. | | | 13.8% |
| 40° C. | | | 16.0% |
| Homodimer of the FGF21 protein of SEQ ID NO: 9 | | | |
| 10 mM Citrate pH7, 150 mM NaCl | 0.9% | 1.4% | |
| 4° C. | | | 3.3% |
| 25° C. | | | 3.3% |
| 40° C. | | | 5.5% |
| Homodimer of the FGF21 protein of SEQ ID NO: 5 | | | |
| 10 mM Citrate pH7, 150 mM NaCl | 0.4% | 1.4% | |
| 4° C. | | | 2.9% |
| 25° C. | | | 3.3% |
| 40° C. | | | 5.4% |

EXAMPLE 7

Physical Stability

Self-Association

Purified FGF21 protein of SEQ ID NO: 7 (which is the FGF21 protein of SEQ ID NO: 5 having D98L) and purified FGF21 protein of SEQ ID NO: 6 (which is the FGF21 protein of SEQ ID NO: 5 having K100L) were dialyzed into 10 mM Citrate, 50 mM NaCl, pH6 buffer and concentrations are determined to be 12.9 mg/mL, 1.0 mg/mL, and 0.6 mg/mL, respectively. Each recovered sample from dialysis is analyzed by SEC to determine the % HMW (Table 5). The % HMW was <1% for all recovered dialysates. Next, samples are concentrated to 65-87 mg/mL using a 10,000 molecular weight cut-off, 4 mL Millipore spin concentrator. The concentrations for each sample are shown in Table 5. After concentration, the % HMW is determined again by SEC using the concentrated protein.

As shown in Table 5, the % HMW for the homodimer of the FGF21 protein of SEQ ID NO: 5 increased to 2.3% indicating a low level of self-association that occurred at higher concentrations. In contrast, the % HMW for the homodimer of the FGF21 protein of SEQ ID NO: 7 (which is the FGF21 protein of SEQ ID NO: 5 having D98L) and the homodimer of the FGF21 protein of SEQ ID NO: 6 (which is the FGF21 protein of SEQ ID NO: 5 having K100L) increased to levels of 8.0% and 14.2%, respectively. These data demonstrate a higher propensity for undesirable self-association when wild type L98 or L100 is included in the sequence. Thus, both L98D and L100K substitutions contribute to a decrease the self-association of the FGF21 protein of SEQ ID NO: 5. Furthermore, it is concluded that the presence of L100K in the absence of L98D (i.e. the FGF21 protein of SEQ ID NO: 7) is insufficient to fully minimize self-association. Conversely, it is concluded that the presence of L98D in the absence of L100K (i.e. the FGF21 protein of SEQ ID NO: 6) is insufficient to fully minimize self-association. Thus, the maximum effect on reducing self association requires both L98D and L100K together.

Upon dilution of concentrated proteins to 1 mg/mL, the % HMW decreases demonstrating that the self-association is reversible. Dilution of the homodimer of the FGF21 protein of SEQ ID NO: 6 (which is the FGF21 protein of SEQ ID NO: 5 having K100L) to 1 mg/mL results in the % HMW decreasing from 14.2% to 2.0%. Dilution of the homodimer of the FGF21 protein of SEQ ID NO: 7 (which is the FGF21 protein of SEQ ID NO: 5 having D98L) to 1 mg/mL results in the % HMW decreasing from 8.0% to 1.3%. When L98D and L100K are present together in the homodimer of the FGF21 protein of SEQ ID NO: 5, the % HMW decreases to 0.88% upon dilution to 1 mg/mL, again demonstrating the more beneficial behavior when L98D and L100K are combined.

TABLE 5

Self-Association

| FGF21 Protein | Dialysate | | Concentrate | | Concentrate Diluted to 1 mg/mL | |
|---|---|---|---|---|---|---|
| | mg/mL | % HMW | mg/mL | % HMW | mg/mL | % HMW |
| Homodimer of the FGF21 protein of SEQ ID NO: 5 | 12.9 | 0.75 | 76 | 2.3 | 1.0 | 0.88 |
| Homodimer of the FGF21 protein of SEQ ID NO: 6 | 0.6 | 0.78 | 87 | 14.2 | 1.0 | 2.0 |
| Homodimer of the FGF21 protein of SEQ ID NO: 7 | 1.0 | 0 | 65 | 8.0 | 1.0 | 1.3 |

EXAMPLE 8

Glucose Lowering in Ob/ob Mouse Model

Male ob/ob mice and age-matched ob/m (lean) controls are 7 weeks of age upon arrival and 8-9 weeks of age at initiation of treatment. Upon arrival, all mice are single housed and allowed to acclimate for 1-2 weeks before the start of treatment. The mice are fed Purina Rodent Chow 5015 and given house water from an auto-water apparatus ad libitum. The mice are housed in 12-hour light/dark cycle with ambient temperature set at 75° F. One to two days prior to initiation of treatment, blood samples are collected via tail bleed. Blood glucose levels are measured using an Accu-Check Avivia blood glucose meter (Roche) and serum samples are collected for the assay of insulin using the Meso Scale mouse/rat insulin assay kit. On the day of treatment initiation (day 0), the mice are sorted into groups based on the pretreatment body weight, blood glucose, and serum insulin (BRAT sorting software). On day 0 and day 3, mice are dosed SQ with 0.1 to 30 nmol/kg of the homodimer of the FGF21 protein of SEQ ID NO: 5, in a volume of 10 ml/kg. Dosing vehicle is sterile PBS (HyClone DPBS/Modified-Calcium-Magnesium) containing 0.03% mouse serum albumin (MSA; Sigma A3139). Blood glucose is measured daily for 7 days and the AUC is determined. $ED_{50}$ calculations for the glucose lowering are based on the AUC. Liver homogenates are collected at the time of sacrifice and liver triglycerides are measured on the Hitachi Modular P clinical analyzer.

On day 7, vehicle treated mice were hyperglycemic with mean blood glucose levels measured at 387±63.0 mg/dl (mean±SEM), while ob/m lean control mice had blood glucose levels of 162±9.0 mg/dl (mean±SEM). The homodimer of the FGF21 protein of SEQ ID NO: 5 lowered blood glucose to levels comparable to the ob/m lean controls. The $ED_{50}$ of the homodimer of the FGF21 protein of SEQ ID NO: 5 was 2.796 nmol/kg (95% confidence interval=1.1-7.0).

We claim:

1. An FGF21 protein consisting of a first polypeptide fused to a second polypeptide via a linker, wherein:
    a.) the first polypeptide consists of an IgG4 Fc portion,
    b.) the second polypeptide has the amino acid sequence of SEQ ID NO: 1, and
    c.) the linker fuses the C-terminus of the first polypeptide to the N-terminus of the second polypeptide.

2. The FGF21 protein of claim 1, wherein the IgG4 Fc portion has the amino acid sequence of SEQ ID NO: 14.

3. An FGF21 protein having the amino acid sequence (SEQ ID NO: 5)
ESKYGPPCPPCPAPEAAGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGGGGSGGGGSGGGGSAHPIPDS

SPLLQFGGQVRQRYLYTDDAQQTECHLEIREDGTVGCAADQSPESLLQLK

ALKPGVIQILGVKTSRFLCQRPDGALYGSLHFDPEACSFREDLKEDGYNV

YQSEAHGLPLHLPGDKSPHRKPAPRGPARFLPLPGLPPALPEPPGILAPQ

PPDVGSSDPLRLVEPSQLRSPSFE.

4. A homodimer of two FGF3 proteins of claim 3.

5. The homodimer of claim 4, wherein each FGF21 protein is glycosylated.

6. A pharmaceutical composition comprising the homodimer of claim 5, and at least one pharmaceutically acceptable carrier, diluent, or excipient.

7. A method of lowering blood glucose in a patient having type 2 diabetes, obesity, dyslipidemia, or metabolic syndrome, comprising administering a homodimer of claim 5 to a patient in need thereof.

8. A DNA molecule encoding an FGF21 protein, wherein the FGF21 protein has the amino acid sequence of SEQ ID NO: 5.

9. A mammalian host cell transformed with the DNA molecule of claim 8, which cell is capable of expressing an FGF21 protein, wherein the FGF21 protein has the amino acid sequence of SEQ ID NO: 5.

10. A process for producing a homodimer of two FGF21 proteins comprising the steps of:
    i) cultivating a mammalian host cell comprising a polynucleotide encoding a FGF21 protein having the amino acid sequence of SEQ ID NO: 5 under conditions such that said FGF21 protein is expressed; and
    ii) recovering from said host cell the homodimer wherein the amino acid sequence of each FGF21 protein is SEQ ID NO: 5.

* * * * *

UNITED STATES PATENT AND TRADEMARK OFFICE
CERTIFICATE OF CORRECTION

PATENT NO. : 8,741,841 B2
APPLICATION NO. : 13/910149
DATED : June 3, 2014
INVENTOR(S) : Ryan James Darling Page 1 of 1

It is certified that error appears in the above-identified patent and that said Letters Patent is hereby corrected as shown below:

In the Claims:

At Column 40, Line 10, In Claim 4, delete "FGF3" and insert -- FGF21 --, therefor.

Signed and Sealed this
Ninth Day of September, 2014

Michelle K. Lee
*Deputy Director of the United States Patent and Trademark Office*